United States Patent [19]

Gunther

[11] 3,971,742

[45] July 27, 1976

[54] ORGANO-CHALCOGEN COMPOSITIONS

[75] Inventor: Wolfgang H. H. Gunther, Webster, N.Y.

[73] Assignee: Xerox Corporation, Stamford, Conn.

[22] Filed: Dec. 13, 1973

[21] Appl. No.: 424,496

Related U.S. Application Data

[60] Continuation-in-part of Ser. No. 210,275, Dec. 20, 1971, Pat. No. 3,905,958, which is a division of Ser. No. 59,495, July 30, 1970, Pat. No. 3,671,467.

[52] U.S. Cl. .............................. 260/2 M; 96/1 PC; 96/1.5; 260/239 R; 260/607 R
[51] Int. Cl.² ......................................... C08G 79/14
[58] Field of Search ............ 260/2 M, 607 R, 239 R

[56] References Cited

UNITED STATES PATENTS

| | | | |
|---|---|---|---|
| 2,500,164 | 3/1950 | Garwood et al. | 260/607 R |
| 3,671,467 | 6/1972 | Gunther | 260/2 M |

Primary Examiner—Wilbert J. Briggs, Sr.
Attorney, Agent, or Firm—James J. Ralabate; Michael H. Shanahan; John H. Faro

[57] ABSTRACT

Photoconductive composition comprising an organo-chalcogen polymer of the formula:

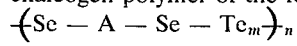

wherein

A is a member selected from the group consisting of an alkylene radical having from about 9 to about 20 carbon atoms, a divalent aromatic radical having from about 6 to about 50 carbon atoms and a divalent heterocyclic radical;

$m$ is at least 1; and $n$ is at least 2 or

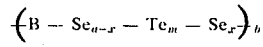

wherein

B is a member selected from the group consisting of divalent hydrocarbylene radicals and divalent heterocyclic radicals;

$a$ is a positive integer of at least 2;

$x$ is a positive integer of at least 1 but less than $a$;

$m$ is a positive integer in excess of 1; and $b$ is a positive integer in excess of 1.

This composition possesses enhanced spectral response and electrophotographic speed over compositions containing selenium alone. Compositions of this type are, thus, especially suitable for use in high speed electrophotographic imaging systems wherein rapid cycling of the photoresponsive member is essential.

3 Claims, No Drawings

ORGANO-CHALCOGEN COMPOSITIONS

CROSS REFERENCE TO RELATED APPLICATIONS

This application is a continuation-in-part of application Ser. No. 210,275, filed Dec. 20, 1971, now U.S. Pat. No. 3,905,958, which in turn is a divisional of application Ser. No. 59,495, filed July 30, 1970 (now U.S. Pat. 3,671,467, issued June 20, 1972).

BACKGROUND OF THE INVENTION

1. Field of the Invention

This invention relates to a photoconductive composition, articles prepared from this composition and methods of use of said articles. More specifically, this invention involves organo-chalcogen compositions, electrophotographic imaging members wherein the photoconductive insulating layer comprises an organo-chalcogen composition, and an electrophotographic imaging process employing said imaging member.

2. Description of the Prior Art

The formation and development of images on the imaging surfaces of photoconductive materials by electrostatic means is well known. The best known of the commercial processes, more commonly known as xerography, involves forming a latent electrostatic image on the imaging layer of an imaging member by first uniformly electrostatically charging the surface of said layer and then exposing this electrostatically charged surface to a light and shadow image. The light struck areas of the imaging layer are thus rendered conductive and the electrostatic charge selectively dissipated in these irradiated areas. After the photoconductor is exposed, the latent electrostatic image on this image bearing layer is rendered visible by development with a finely divided colored electroscopic material, known in the art as "toner". This toner will be principally attracted to those areas on the surface of the imaging layer which retain the electrostatic charge and thus render visible the latent image.

The developed image can then be read or permanently affixed to the photoconductor where the imaging surface is not to be reused. This latter practice is usually followed with respect to the binder type photoconductive films (e.g. zinc oxide pigment dispersed in a film forming insulating resin) where the photoconductive imaging layer is also an integral part of the finished copy.

In so-called "plain paper" copying systems, the latent image can be developed on a reusable photoconductive layer or transferred to another surface, such as a sheet of paper, and thereafter developed. When the latent image is developed on the imaging surface of a reusable photoconductive layer, it is subsequently transferred to another substrate and then permanently affixed thereto. Any one of a variety of well known techniques can be used to permanently affix the toner image to the copy sheet, including overcoating with transparent films, and solvent or thermal fusion of the toner particles to the supportive substrate.

In the above "plain paper" copying systems, the materials used in the photoconductive layer should preferably be capable of rapid switching from insulative to conductive to insulative state in order to permit cyclic use of the imaging layer. The failure of the material to return to its relatively insulative state prior to succeeding charging sequence will result in a decrease in the maximum charge acceptance of the photoreceptor. This phenomenon, commonly referred to in the art as "fatigue", has in the past been avoided by the selection of photoconductive materials possessing rapid switching capacity. Typical of the materials suitable for use in such a rapidly cycling imaging system include anthracene, sulfur, selenium and mixtures thereof (U.S. Pat. No. 2,297,691); selenium being preferred because of its superior photosensitivity. In order to further enhance the spectral range and/or electrophotographic response of selenium, selenium has been alloyed with materials such as tellurium and arsenic, U.S. Pat. Nos. 2,745,327 (Te/Se); and 2,803,542 (As/Se); 2,822,300 (As/Se); 3,312,548 (As/Sd & halogen).

Although selenium and selenium alloys probably are the most desirable materials from which to fashion the imaging layer of a photoconductive imaging member, imaging layers of these materials do have some serious physical limitations. For example, imaging layers of amorphous selenium and selenium alloys are sensitive to abrasion. Moreover, the adhesion of vacuum deposited selenium on many of the conductive substrates used in electrophotography is relatively poor. Poor adhesion of imaging layers prepared from such materials does not, however, cause impairment of the integrity of the imaging member so long as the conductive substrate bearing this imaging layer is inflexible. Recently, there has been increasing interest in the use of flexible photoconductors due to the greater freedom in machine design and increased speed in copier throughput permitted by the use of such flexible imaging members. Unfortunately, because of the brittle nature of amorphous selenium and selenium alloy imaging layers, coupled with relatively poor adhesion to most conventional conductive substrates, such materials do not readily lend themselves to fabrication of flexible imaging members since repeated flexure of the member can result in cracking and separation of the imaging layer from the conductive substrate.

One technique suggested for the resolution of this problem is the provision of an interfacial layer intermediate between the conductive substrate and an imaging layer of amorphous selenium or selenium alloy, U.S. Pat. Nos. 3,713,821 and 3,671,467 (of which the instant application is a continuation-in-part). These interfacial layers reportedly provide improved adhesion between the imaging layer and the conductive substrate. The interlayer disclosed in '467 comprises a polymeric seleno-organic material having recurring units of the formula

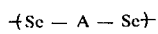

wherein
A is a member selected from the group consisting of an alkylene radical having from 9 to 50 carbon atoms, a divalent aromatic or a substituted aromatic radical having from 6 to 50 carbon atoms and heterocyclic radicals.

or

wherein
B is a member selected from the group consisting of a divalent hydrocarbylene radical and a divalent heretocyclic radical;
a is a positive integer of at least 3; and $b$ is a positive integer greater than 1.

Although many of the polymers having recurring units of formula I and all of the polymers having recurring units of formula II are reportedly intrinsically photoconductive, the spectral response and electrophotographic speed of such materials is somewhat limited.

Accordingly, it is the object of this invention to provide a polymeric photoconductive composition free from the limitations possessed by the above materials.

More specifically, it is the object of this invention to provide a polymeric photoconductive material having enhanced abrasion resistance.

Another object of this invention is to provide a polymeric photoconductive composition suitable in preparation of flexible photoconductive imaging members by virtue of its enhanced adhesion to flexible conductive substrates.

Yet another object of this invention is to provide a polymeric photoconductive composition having enhanced spectral response and a more rapid rate of light discharge.

Still yet another object of this invention is to provide a method for controlling the photoresponse of organoselenium polymers and a method for controlling the photoresponse of tellurium.

A further object of this invention is to provide a polymeric photoconductive composition which readily lends itself to a continuous process for the manufacture of electrophotographic imaging members.

Still further objects of this invention include providing flexible electrophotographic imaging members prepared from the above photoconductive compositions and imaging processes using such flexible imaging members.

SUMMARY OF THE INVENTION

The above and related objects are achieved by providing an organo-chalcogen photoconductive composition comprising a polymer having recurring units of the formula:

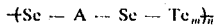

wherein
- A is a member selected from the group consisting of an alkylene radical having from about 9 to about 20 carbon atoms, a divalent aromatic radical having from about 6 to about 50 carbon atoms and a divalent heterocyclic radical;
- $m$ is at least 1; and
- $n$ is at least 2.

or

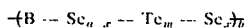

wherein
- B is a member from the group consisting of a divalent hydrocarbylene radical and a divalent heterocyclic radical
- $a$ is a positive integer of at least 2;
- $x$ is a positive integer of at least 1 but less than $a$;
- $m$ is a positive integer in excess of 1; and
- $b$ is a positive integer in excess of 1.

DESCRIPTION OF THE INVENTION INCLUDING PREFERRED EMBODIMENTS

The polymeric organo-chalcogen compositions of this invention can be prepared by fusing an intimate mixture of tellurium with at least one of the compounds having the following formulae:

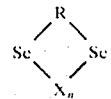

wherein
- R is selected from divalent hydrocarbylene radicals of from 5 to 50 carbon atoms, divalent heterocyclic, alicyclic and aromatic radicals having from 3 to 50 carbon atoms;
- $n$ is a positive integer; and
- $x$ is the radical —Se—R—Se—; or linear polymers comprising recurring units represented by the formula:

wherein
- A is selected from the group consisting of divalent alkylene radicals having at from 9 to 20 carbon atoms, divalent aromatic radicals having from 6 to 50 carbon atoms and divalent heterocyclic radicals or

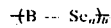

wherein
- B is selected from the group consisting of divalent hydrocarbylene radicals and divalent heterocyclic radicals,
- $a$ is a positive integer of at least 3 and
- $b$ is a positive integer greater than 1.

Subsequent to introduction of tellurium into the polymer backbone, said polymer can be cast or coated on an appropriate (preferably flexible) substrate. Alternatively, the polymeric chalcogen composition can be formed directly on the substrate and once in the molten state evenly spread so as to provide a layer of substantially uniform thickness.

Compounds I and III can be prepared by reacting a difunctional organic compound of the formula:

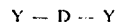

wherein
- D is selected from a member of the group consisting of a divalent hydrocarbylene and a divalent heterocyclic radical, and
- Y is readily displaceable member selected from the group consisting of halides, epoxy or sulfonate esters and diazonium halides in which both reactive sites are capable of forming a covalent bond with a molecule containing a diselenide (—Se — Se —) precursor. Representative diselenide precursors include bis(selenosulfate), bis(selenocyanate), bis(selenols), and bis(selenoesters). Compound II can be prepared simply by fusion of elemental selenium with compound I and III wherein the organic divalent radicals R and A of said compounds are defined as the divalent radical B of compound II.

Compounds I, II and III used in preparation of the organo-chalcogen compositions of this invention are disclosed and methods for their preparation described in U.S. Pat. No. 3,677,467, which is hereby incorporated by reference.

Preliminary to forming a melt from the tellurium (hereinafter also referred to as "inorganic ingredient") with one or more of compounds I, II and III (hereinafter also referred to as "organic ingredients"), the ingredients of the melt are physically ground together until formation of an intimate admixture therebetween. Ordinarily, the relative concentration of inorganic ingredients to organic ingredients in such admixture can range from about 1:1 to about 12:1. The conductive substrate upon which such polymer is coated or formed can be almost virtually any of the materials presently in use in electrophotographic imaging members, provided such materials are thermally stable at temperatures required to render the organo-chalcogen composition molten. In organo-chalcogen compositions having relatively low loadings of inorganic materials, traditional solvent casting techniques can be used in forming photoconductive films from such compositions. With regard to these latter materials, the thermal stability of the substrate is not a critical feature, thus, enabling use of many of the conductive substrates, such as plastics and paper, traditionally used in formation of electrophotographic imaging members. The amount of polymeric organo-chalcogen composition imparted to said substrate should be sufficient to provide a substantial uniform layer having a dry film thickness of from about 1 to about 200 microns. The ability to incorporate tellurium into organo-selenium polymers provides a unique method for reducing the rate of dark discharge of tellurium while simultaneously increasing the rate of light discharge and range of spectral response of organo-selenium polymers. The organo-chalcogen polymeric composition resulting from the introduction of tellurium into organo-selenium polymers is a highly responsive photoconductor having excellent adhesion to flexible conductive substrates and is also suitable in providing an adhesive rectifying interface between a photoconductive insulating layer of selenium or selenium alloy and such conductive substrate.

In another embodiment of this invention, the organo-chalcogen composition can be employed as a binder for other photoconductive pigments. A number of the organo-chalcogen compositions of this invention possess extensive aromatic functionality and are, thus, capable of rapid and efficient transport of charge carriers generated within the bulk of this material. Any one of a number of photoconductive pigments can be dispersed in the polymeric organo-chalcogen composition of this invention and the resulting dispersion cast or coated on a conductive substrate. The relative concentration of such pigment within the organo-chalcogen binder will vary depending upon its carrier generating efficiency and the degree of aromatic functionality of the organo-chalcogen binder. In the preferred binder-photoconductive insulating layer systems of this invention, the photoconductive pigment is primarily responsive to activating electromagnetic radiation beyond the range of substantial photoresponse of the organo-chalcogen binder and the organo-chalcogen binder has a high degree of aromatic functionality. In such a preferred system, the concentration of photoconductive pigment generally need not exceed about 10 weight percent in order to provide a photoconductive composition having satisfactory electrophotographic speed.

In yet another alternative embodiment, this polymeric organo-chalcogen composition can be overcoated on a photoconductive insulating layer. The favorable charge transport properties of this material permits separation of carrier generation and transport functions in the same manner described above. Moreover, because of the superior durability of these polymeric chalcogen compositions, they can provide a highly effective abrasion resistant shield for some of the more abrasion prone photoconductive insulating layers.

The Examples which follow further define, describe and illustrate preparation and use of the polymeric organo-chalcogen compositions of this invention. Techniques and apparatus used in preparation and evaluation of such compositions are standard or, as hereinbefore described. Parts and percentages appearing in such Examples are by weight unless otherwise stipulated.

EXAMPLE I

About 1.5 parts tellurium and 0.5 parts m-xylene-α, α-disenlenide cyclic dimer are placed in a mortar cavity and ground together into a fine powdery mixture with a pestle. This powder is transferred to the surface of a ball grained aluminum plate and the plate gradually heated to about 250°C until the powdery mixture becomes uniformly molten. This melt is then evenly distributed on the surface of the plate with the assistance of a glass rod. This plate is rapidly cooled to avoid crystallization of the molten coating by contacting the uncoated surface of the alluminum plate with a heat sink. Upon cooling, the photoelectric properties of the dark red homogenous organo-chalcogen coating are evaluated by simply charging the coating in the dark to a positive potential by means of a Xerox Model D processor followed by blanket exposure of the sensitized surface of the coating with a 100 Watt incandescent lamp from a distance of 20 centimeters. Substantially complete discharge of the plate is observed within less than 15 seconds from the onset of such exposure. Repeated charging and blanket exposure of the plate gave the following recorded voltage drops:

| CYCLE | INITIAL POTENTIAL | VOLTAGE DROP AFTER 15 SECONDS |
|---|---|---|
| 1 | 540 | 540 |
| 2 | 540 | 540 |
| 3 | 530 | 530 |
| 4 | 540 | 540 |
| 5 | 520 | 520 |
| 6 | 530 | 530 |
| 7 | 540 | 540 |
| 8 | 570 | 570 |
| 9 | 520 | 520 |
| 10 | 570 | 570 |
| 11 | 540 | 540 |
| 12 | 550 | 550 |

The above data demonstrate the good cycling capacity of the photoconductive insulating layers prepared from the polymeric organo-chalcogen composition of this Example.

The organo-chalcogen coating is again sensitized as described above and exposed to image information through a Xerox Model A camera at f/10, (exposure time 7.5 seconds). The latent image thus produced is developed by cascading Xerox 2400 toner and carrier onto the imaging bearing surface of the plate, the toner image transferred to a sheet of paper and fused thereto. The plate is then fully discharged and cleaned of residual toner, whereupon the imaging/development procedure is repeated for several additional cycles; the only variation being the extension of the exposure time from 7.5 seconds up to about 60 seconds. Print quality is acceptable in each instance and some slight decrease in contrast is noted as the exposure time become more prolonged, apparently due to change of the latent image contrast. Comparison of the photoresponse of this organo-chalcogen coated plate with a standard selenium plate indicates that both plates are substantially equivalent (optimum print quality for the selenium plate requiring exposure at f/16 for 12 seconds).

EXAMPLE II

An organo-chalcogen composition is prepared from equal parts tellurium and poly(para phenylene) diselenide in the same manner described in Example I. Evaluation of cycling and imaging capability yields results comparable to those reported in Example I.

EXAMPLE III

An organo-chalcogen composition is prepared from equal parts tellurium and poly(1,4-napthalene) diselenide in the same manner described in Example I. Evaluation of cycling and imaging capability yields results comparable to those reported in Example I.

EXAMPLE IV

An organo-chalcogen composition is prepared from equal parts tellurium and poly(9,10-anthracene) diselenide in the same manner described in Example I. Evaluation of cycling and imaging capability yields results comparable to those reported in Example I.

What is claimed is:

1. A method for controlling the photoresponsiveness of tellurium comprising fusion of intimate mixture of tellurium with at least one compound of the formula:

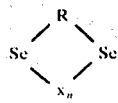

wherein
R is selected from divalent hydrocarbylene radicals of from 5 to 50 carbon atoms, divalent heterocyclic, alicyclic and aromatic radicals having from 3 to 50 carbon atoms;
$n$ is a positive integer; and
$x$ is the radical —Se—R—Se—; or linear polymers comprising recurring units represented by the formula:

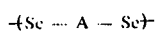

wherein
A is selected from the group consisting of divalent alkylene radicals having from 9 to 20 carbon atoms, divalent aromatic radicals having from 6 to 50 carbon atoms and divalent heterocyclic radicals,
the relative weight ratio of tellurium to cyclic diselenide in the intimate mixture ranging from about 1:1 to about 12:1.

2. A method for controlling the photoresponsiveness of tellurium comprising fusion of an intimate mixture of tellurium with at least one compound of the formula:

wherein
B is selected from the group consisting of divalent hydrocarbylene radicals and divalent heterocyclic radicals,
$a$ is a positive integer of at least 3 and
$b$ is a positive integer greater than 1.
the relative weight ratio of tellurium to polyselenide in the intimate mixture ranging from about 1:1 to about 12:1.

3. A method for controlling the photoresponsiveness of compounds

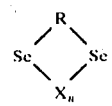

wherein
R is selected from divalent hydrocarbylene radicals of from 5 to 50 carbon atoms, divalent heterocyclic, alicyclic and aromatic radicals having from 3 to 50 carbon atoms;
$n$ is a positive integer; and
$X$ is the radical —Se—R—Se—; or linear polymers comprising recurring units represented by the formula:

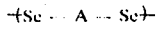

wherein
A is selected from the group consisting of divalent alkylene radicals having at from 9 to 20 carbon atoms, divalent aromatic radicals having from 6 to 50 carbon atoms and divalent heterocyclic radicals
or

wherein
B is selected from the group consisting of divalent hydrocarbylene radicals and divalent heterocyclic radicals,
$a$ is a positive integer of at least 3 and
$b$ is a positive integer greater than 1 comprising fusing an intimate mixture of said compounds and tellurium,
the relative weight ratio of tellurium to the above compounds in said intimate mixture ranging from about 1:1 to about 12:1.

* * * * *